US011614442B2

(12) United States Patent
Rezzi et al.

(10) Patent No.: US 11,614,442 B2
(45) Date of Patent: Mar. 28, 2023

(54) METHOD FOR DETERMINING THE DISTINCTIVE NUTRITIONAL REQUIREMENTS OF A PATIENT

(71) Applicant: SOCIÉTÉ DES PRODUITS NESTLÉ S.A., Vevey (CH)

(72) Inventors: Serge Andre Dominique Rezzi, Semsales (CH); Stephanie Blum-Sperisen, Pully (CH); Magali Faure, Forel (CH); Denis Breuille, Lausanne (CH)

(73) Assignee: Societe des Produits Nestle S.A., Vevey (CH)

( * ) Notice: Subject to any disclaimer, the term of this patent is extended or adjusted under 35 U.S.C. 154(b) by 252 days.

(21) Appl. No.: 16/986,928

(22) Filed: Aug. 6, 2020

(65) Prior Publication Data

US 2020/0378955 A1 Dec. 3, 2020

Related U.S. Application Data

(63) Continuation of application No. 15/544,307, filed as application No. PCT/EP2016/051283 on Jan. 22, 2016, now Pat. No. 10,768,169.

(30) Foreign Application Priority Data

Jan. 23, 2015 (EP) .................................... 15152312

(51) Int. Cl.

| | |
|---|---|
| ***G01N 33/50*** | (2006.01) |
| ***A23L 33/10*** | (2016.01) |
| ***G01N 33/82*** | (2006.01) |
| ***G01N 33/84*** | (2006.01) |
| ***G01N 33/92*** | (2006.01) |
| ***G01N 33/68*** | (2006.01) |
| ***A23L 33/00*** | (2016.01) |
| ***G01N 33/53*** | (2006.01) |
| ***A61K 45/06*** | (2006.01) |

(52) U.S. Cl.

CPC .......... *G01N 33/5091* (2013.01); *A23L 33/10* (2016.08); *A23L 33/40* (2016.08); *A61K 45/06* (2013.01); *G01N 33/50* (2013.01); *G01N 33/5308* (2013.01); *G01N 33/6803* (2013.01); *G01N 33/6806* (2013.01); *G01N 33/6848* (2013.01); *G01N 33/6893* (2013.01); *G01N 33/82* (2013.01); *G01N 33/84* (2013.01); *G01N 33/92* (2013.01); *A23V 2002/00* (2013.01); *G01N 2333/90254* (2013.01); *G01N 2800/02* (2013.01); *G01N 2800/065* (2013.01); *G01N 2800/7009* (2013.01)

(58) Field of Classification Search

CPC ............... G01N 33/5091; G01N 33/50; G01N 33/5308; G01N 33/6803; G01N 33/6806; G01N 33/6848; G01N 33/6893; G01N 33/82; G01N 33/84; G01N 33/92; G01N 2333/90254; G01N 2800/02; G01N 2800/065; G01N 2800/7009; A23L 33/10; A23L 33/40; A61K 45/06; A23V 2002/00

See application file for complete search history.

(56) References Cited

U.S. PATENT DOCUMENTS

| | | | |
|---|---|---|---|
| 5,985,339 | A | 11/1999 | Kamaeri |
| 2006/0275909 | A1 | 12/2006 | Spitzer et al. |
| 2007/0087440 | A1 | 4/2007 | Axford |
| 2010/0196880 | A1 | 8/2010 | Satyaraj |
| 2010/0266723 | A1 | 10/2010 | Bralley, III et al. |
| 2011/0256233 | A1 | 10/2011 | Fournell |

FOREIGN PATENT DOCUMENTS

| | | | |
|---|---|---|---|
| JP | H09327269 | A | 12/1997 |
| WO | 2014020004 | | 2/2014 |
| WO | 2014066628 | A2 | 5/2014 |

OTHER PUBLICATIONS

Schnackenberg et al. "Monitoring the health to disease continuum with global metabolic profiling and systems biology" Pharmacogenomics, 2006, vol. 7, No. 7, pp. 1077-1086.

Ates et al. "Serum Ghrelin Levels in Inflammatory Bowel Disease with Relation to Disease Activity and Nutritional Status" Digestive Diseases and Sciences, 2008, vol. 53, pp. 2215-2221.

Hengstermann et al. "Altered status of antioxidant vitamins and fatty acids in patients with inactive inflammatory bowel disease" Clinical Nutrition, 2008, vol. 27, pp. 571-578.

Mijac et al. "Nutritional status in patients with active inflammatory bowel disease: Prevalence of malnutrition and methods for routine nutritional assessment" European Journal of Internal Medicine, 2010, vol. 21, pp. 315-319.

Huang et al. "Mass spectrometry-based metabolomic profiling identifies alterations in salivary redox status and fatty acid metabolism in response to inflammation and oxidative stress in periodontal disease" Free Radical Biology and Medicine, 2014, vol. 70, pp. 223-232.

Brocker, Chad et al. "The role of hyperosmotic stress in inflammation and disease." Biomol. Concepts (2012) 3 345-364. (Year: 2012).

Diamanti, Antonella et al. "Plasma citrulline as surrogate marker of intestinal inflammation in pediatric and adolescent with Crohn's disease: preliminary report." Int. J. Colorectal Dis. (2011) 26 1445-1451. (Year: 2011).

Harries, Anthony D. et al. "Nutritional disturbances in Crohn's disease." Postgraduate Medical Journal (1983) 59 690-697. (Year: 1983).

Hengstermann, Susanne et al. "Altered status of antioxidant vitamins and fatty acids in patients with inactive inflammatory bowel disease." Clinical Nutrition (2008) 27 571-578. (Year: 2008).

(Continued)

*Primary Examiner* — Christopher Adam Hixson
(74) *Attorney, Agent, or Firm* — K&L Gates LLP

(57) ABSTRACT

The present invention relates to a method for determining the distinctive nutritional requirements of a patient with specific nutritional needs and providing a composition meeting the distinctive nutritional requirements of said patient.

18 Claims, 4 Drawing Sheets

(56) References Cited

OTHER PUBLICATIONS

Miralles-Barrachina, 0. et al. "Low levels of glutathione in endoscopic biopsies of patients with Crohn's colitis: the role of malnutrition." Clinical Nutrition (1999) 18 313-317. (Year: 1999).
He et al., "Evaluation of nutritional status in patients with inflammatory bowel disease using mini nutritional assessment and subjective global assessment", May 18, 2011, vol. 19, No., pp. 1529-1533.
Wei, "Enteral nutrition formulation choice in inflammatory bowel disease", Inflammatory bowel disease, 2013, 11 pages.

| | Level in IBD vs. Level in healthy subjects | Enhanced requirement in threonine in IBD |
|---|---|---|
| Threonine oxidation | Lower | Yes |
| Isoleucine oxidation | Similar | |
| Threonine oxidation | Similar or higher | No |
| Isoleucine oxidation | Similar or higher | |

FIG.4

METHOD FOR DETERMINING THE DISTINCTIVE NUTRITIONAL REQUIREMENTS OF A PATIENT

CROSS REFERENCE TO RELATED APPLICATIONS

This application is a continuation of U.S. application Ser. No. 15/544,307 filed Jul. 18, 2017, which is a National Stage of International Application No. PCT/EP2016/051283 filed Jan. 22, 2016, which claims priority to European Patent Application No. 15152312.3 filed Jan. 23, 2015, the entire contents of which are incorporated herein by reference.

FIELD OF INVENTION

The present invention relates to a method for determining the distinctive nutritional requirements of a patient with specific nutritional needs and providing a composition meeting the distinctive nutritional requirements of said patient.

BACKGROUND

A number of parameters or compounds define the nutritional status of a subject. For example, nutrients, micronutrients, and other compounds are found in certain concentrations in a fluid or tissue of the subject. A number of diseases change the concentrations of these compounds or values of these parameters, due to increased utilization of these compounds to fight against the disease, metabolic changes, and/or suboptimal dietary management of the patient. As a result the subject suffering from such a disease is malnourished because the relevant parameters and compounds are no longer in the range found in a healthy subject and lead to nutritional deficiencies, like improper provision of structural components, insufficient energy supply, or a lack of functional components. Thus, the subject suffering from a disease affecting the nutritional status can benefit from a nutritional intervention addressing the distinctive nutritional requirements of said subject. Providing the subject with a nutritional composition comprising nutrients and micronutrients in amounts that reestablish the metabolic, physiologic and functional equivalence of the nutritional status of a healthy subject would therefore be required.

A particular example of such a disease where the subject exhibits distinctive nutritional requirements is inflammatory bowel disease (IBD).

The role of nutrition in IBD gathers high interest, especially in pediatric Crohn's Disease (CD), where studies have shown that exclusive enteral nutrition (EEN) can induce remission in mild to moderate disease comparable to corticosteroids. Thus, nutritional interventions offered in addition to the standard of care (SoC) are an appealing option for a safe long-term disease management. Malnutrition is common in pediatric and adult patients with IBD, especially in those with CD, and typically manifests as protein-energy deficit yielding to general weight loss, and/or vitamin/mineral deficiencies. In general, poor dietary intake secondary to postprandial abdominal pain and diarrhea is the most common cause of malnutrition in IBD. The degrees of malnutrition depend on the duration, severity and extend of the disease, as well as loss of function due to bowel resection or fibrosis. IBD patients have also been reported to have fat and muscle mass depletion; and micronutrient deficiencies also occur with mild disease or in remission phase.

Beyond malnutrition associated nutrient deficiencies, nutrition is also considered as an effective approach to the maintenance of the remission phase and particularly to maintain the mucosal health. Intestinal mucins forming the mucus gel and protecting the intestinal epithelium have been suggested of crucial importance to restore epithelial health after mucosal injury in IBD. The body capacity to maintain adequate mucin synthesis is directly related to the bioavailability of some specific amino acids. Intestinal inflammation is known to increase gastrointestinal threonine uptake and mucin synthesis in enterally fed minipigs. Therefore, under inflammatory conditions as in IBD, specific amino acids could become conditionally essential to sustain mucin synthesis justifying thus for their nutritional specific enrichment.

Accordingly, there is the need for a method identifying the distinctive dietary needs of patients suffering from a disease(s) or clinical condition, with a nutritional status that is different from the nutritional status of a healthy subject.

SUMMARY

It is an object of the invention to provide a new method for determining the distinctive dietary needs of a patient with a nutritional status that is different from the nutritional status of a healthy subject.

The invention relates to an in vitro method for determining the distinctive disease related nutritional requirements of a subject suffering from a disease by: a) first determining in a sample of a subject suffering from the disease a profile of the statuses of markers (including nutrients, micronutrients and/or their metabolites, and/or or biomarkers, or any combination thereof) otherwise referred to as a "nutritional profile"; b) second determining in a sample from a healthy subject or from a patient with a different severity or stage of the disease, a similar nutritional profile of the statuses of the same markers (e.g. the same nutrients, micronutrients and/or their metabolites and/or biomarkers) determined in step a)., and c) third comparing the nutritional profiles determined in step a). and b)., and thereby determining the distinctive nutritional requirements for a patient suffering from the disease The method makes it possible to determine the nutritional profile, and distinct nutritional requirements, of patients suffering from a particular disease, and of patients with different levels of severity, or at different stages, of a same disease. Based on these identified nutritional requirements a nutritional composition can be manufactured comprising nutrients and micronutrients in an amount capable of restoring or improving the nutritional profile of the patient suffering from the disease towards the nutritional profile of a healthy subject.

Nutritional compositions are provided comprising nutrients and micronutrients in an amount capable of reestablishing, in the patient suffering from the disease, the nutritional profile of a healthy subject, or a of patient with an improved condition (i.e. lower disease severity).

BRIEF DESCRIPTION OF THE FIGURES

In FIG. 1, "NP" is nutritional profile; "Da" is high disease activity or severity or latest disease stage; "Db" is low disease activity or severity or early disease stage; "Dc" is disease free or healthy condition; "≠" is difference in Nutritional Profile; and "NP(Da)", "NP(Db)", "NPDc" are the Nutritional profiles of Da, Db and Dc respectively.

In FIG. 1, "NP" is nutritional profile; "Da" is high disease activity or severity or latest disease stage; "Db" is low disease activity or severity or early disease stage; "Dc" is disease free or healthy condition; "≠" is difference in Nutritional Profile; and "NP(Da)", "NP(Db)", "NPDc" are the Nutritional profiles of Da, Db and Dc respectively.

FIG. 4. Determining threonine specific requirements in IBD through comparative analysis of threonine and other amino acid oxidation index

DEFINITIONS

"Nutritional status" relates to the quantifiable body status of a person or a population group (cohort). The nutritional status relates to their state of nourishment (the consumption and utilization of nutrients). In the present invention, the nutritional status is quantified using markers indicative of said nutritional status, in particular, biological, biochemical, physiological markers, or other markers determined in a sample of a subject.

"A nutritional profile" relates to a set of quantitative measurements of nutrients and micronutrients or of their relative status markers that are to be determined in a sample (biological fluids such as blood red blood cells, blood plasma, blood serum, urine, tissue . . . ), and thus requires that measurements of several, at least, two nutrients, micronutrients or relative status markers is determined.

A "marker" is a quantifiable parameter that represents one parameter/marker in a profile or set of markers. The quantification of said marker is the status of said marker. This parameter can directly relate to the amount of a certain compound, like a nutrient (e.g. protein, amino acid etc.) or a micronutrient (vitamin, element including mineral etc.). The marker can, however, also relate to a value that is derived from the mathematical combination of nutrient and micronutrient concentrations and/or status markers in the sample. The marker can also be functional markers, and inter alia relate to certain physiological activities (e.g. enzyme activity) or physiological status (oxidative stress status).

"Distinctive nutritional requirements" (DNR) are those nutritional requirements that differ in a diseased subject and a healthy subject. For example, in the sample of a diseased subject the nutritional profile or the quantitative analysis of a profile of nutrients might be different compared to the nutritional profile of a healthy subject. Under such circumstances, the observed differences in the nutritional profile can be used to identify and quantify disease-specific nutrient requirements.

"Amino acids in free form" are amino acids that are comprised in a composition as free amino acids not bound to other compounds, like other amino acids, and are thus not contained in peptides or proteins.

Hence, "amino acids in bound form" are amino acids being part of peptides, proteins, or bound to other compounds.

"Protein amino acids" are those amino acids that are found in naturally produced proteins, including those that are used by the translation machinery to produce proteins and those that that are modified in proteins subsequently to translation.

"Non-protein amino acids" are those amino acids that are not found in naturally produced proteins but which are metabolites or structural components in cells and organisms.

DETAILED DESCRIPTION OF THE INVENTION

The section headings serve to clarify the subject matter and should not be interpreted to limit the subject matter.

Figure 1:
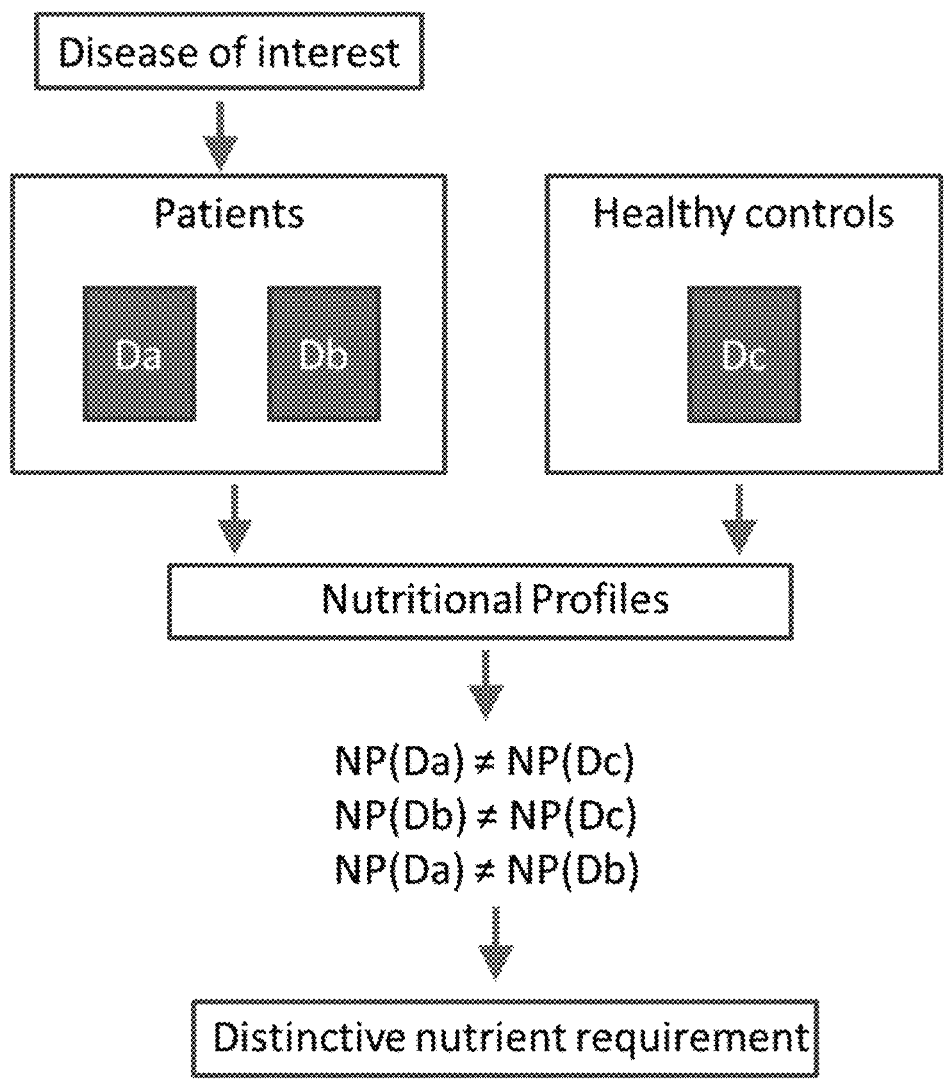
FIG. 1. Diagram displaying the methodological approach towards defining distinctive nutritional requirements. Nutritional profile or nutritional status is used to quantify distinctive nutritional/nutrient requirements associated with a particular disease. Nutritional profile is indicative of overall nutritional status and is measured through a series of nutrient and micronutrient values and/or their related status markers that are measured across patients and healthy populations. Nutritional profile can be correlated with clinical information (including clinical markers) relative to the state of the disease (relapse, remission, degree of severity). Nutritional profiles are compared between patient and healthy groups, and/or within patient groups defined relatively to disease activity, severity or stage. If differences in nutritional profiles are observed between patients and healthy controls, then distinctive nutritional/nutrient requirement (DNR) is defined.

The concept of the invention is illustrated by FIG. 1.

The nutritional profile of a subject suffering from a disease (diseased subject, patient), e.g. in a cohort of patients, is determined and compared to the nutritional status of a cohort of healthy subjects (healthy controls). The nutritional profile encompasses the determination of a profile (with at least two measurements) of nutrients, micronutrients, and/or nutrient/micronutrient status markers. The status of particular markers (quantification of said markers) is determined in a sample of the healthy subject and the patient suffering from the disease. The comparison of the nutritional profiles of patients with the nutritional profiles of healthy subjects serves to identify differences in the levels of nutrients and/or their relative status markers between diseased subjects and healthy controls that are used to identify and quantify distinctive nutritional requirement in the diseased population. In addition, the comparison of nutritional profiles within a patient population stratified relatively to the degree of severity or stage of a disease enables to identify set of nutrients and micronutrients that are associated with lower disease activity or severity or stage, associating this with improved clinical condition of the patients.

In the next step, it is possible to formulate nutritional compositions (products) that take into account the respective distinctive nutritional requirements. In addition, variations of the nutritional profile within a diseased patient population stratified relatively to the degree of severity or stage of the disease is also used to determine nutritional compositions (products) that aim to restore nutritional profiles of patients with higher disease activity or severity towards values of nutritional profiles of patients with lower disease activity or severity.

Figure 2:
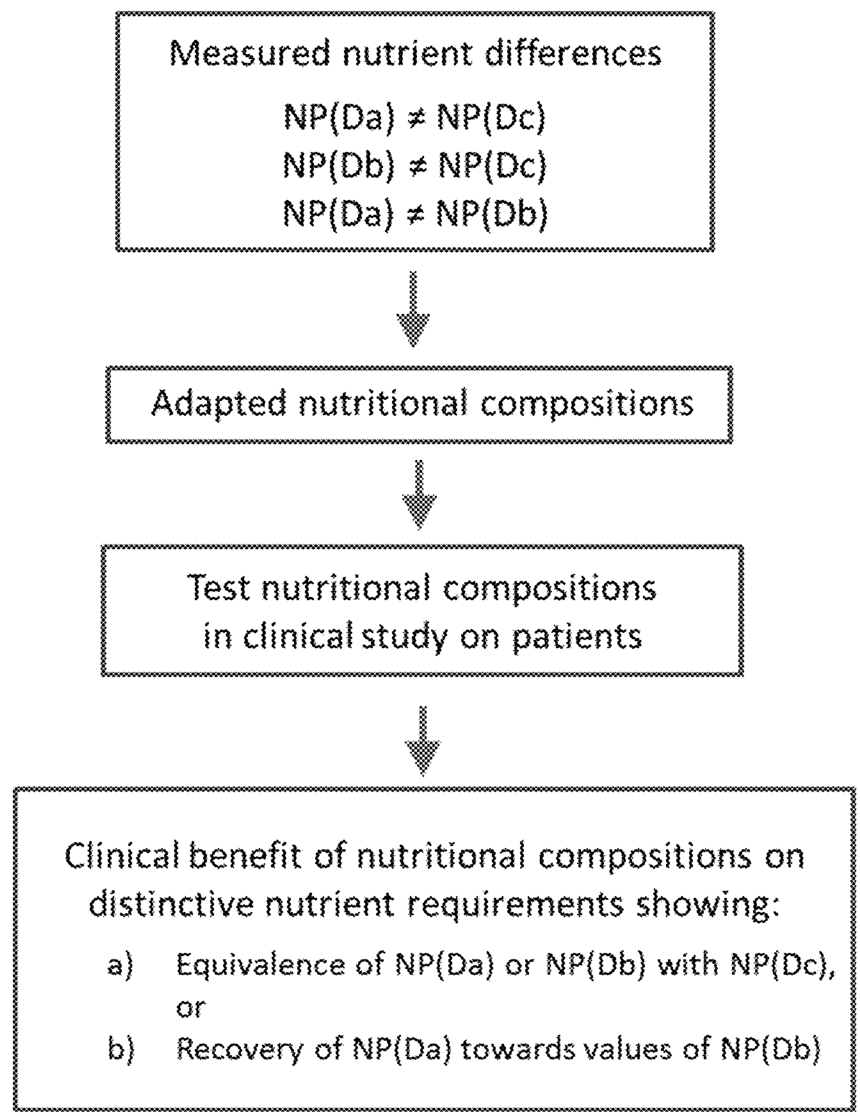
FIG. 2. Diagram illustrating figuratively use of DNR to nutritional composition of a product that aims at recovering nutrient levels as appropriate to alleviate symptoms, sustain remission and improve quality of life of patients with a clinically proven efficacy.

For example, in a patient where a reduced blood level of the amino acid threonine has been observed, and/or alterations in the level of one or more of its oxidation metabolite(s) (FIG. 3), relative to values of threonine, and/or its oxidation metabolite(s), in healthy subjects, the nutritional composition will either contain proteins, peptides in order to adjust the dietary supply of threonine, or the free amino acid threonine itself (FIG. 2). Said composition is to be administered to the patient with the aim to enable the patients to match their specific requirement for threonine. In this way, an increased demand of the diseased subject for threonine is met and the eventual deficiency with respect to threonine is corrected.

Some diseases display different degrees of severity with associated different nutritional needs. In such a case, the cohort of patients where the nutritional status is to be determined will be a cohort of patients displaying the same or similar severity grade of the disease. In this way, it is possible to identify the distinctive nutritional requirements for patients with a particular severity grade of the disease and thus provide products adapted to that severity degree. The method will now be described in more details.

Method for determining the distinctive nutritional requirements of a diseased subject:

The invention relates an in vitro method for determining the distinctive disease related nutritional requirements of a subject suffering from a disease characterized by distinctive nutritional requirements in the diseased subject over a healthy subject comprising the steps:

a. Determining in a sample of a patient suffering from the disease a profile of statuses of markers (including nutrients, micronutrients and/or their metabolites and/or biomarkers), indicating the nutritional profile of said patient, b. Determining in a sample of a healthy subject a profile of the statuses of the same markers determined in step a, indicating the nutritional profile of the healthy subject, c. Comparing the profiles determined in step a. and b., and thereby determining the distinctive nutritional requirements for nutrients in a patient suffering from the disease.

Various nutrients, micronutrients, and their relative metabolites of status markers can be determined (quantified). For each marker its status is determined, i.e. the presence of said marker or its value. Metabolic inter-connected nutrients, micronutrients or related markers can be grouped for an integrated analysis and interpretation.

Depending on the determined nutritional profiles certain nutrient and micronutrient deficiencies can be identified in the diseased patient. The identification of these deficiencies then allows to provide a set of adequate nutrients or micronutrients in the nutritional composition with levels properly adjusted to compensating those deficiencies. Administering this set of nutrients to the diseased subject can have the effect that the nutritional profile in the diseased subject is recovered towards the nutritional profile a healthy subject.

The markers indicating the nutritional status of nutrients can be direct or indirect markers. Direct markers indicate, for example, the amount of nutrients or micronutrients. Indirect markers can be derived from directly determined markers, e.g. by their combination, or can be metabolites or catabolites of the nutrients or micronutrients, and/or biomarkers or catabolites of the nutrients or micronutrients; or can relate to a particular physiological state in the body.

The indirect markers can relate to the determination of the relative status of the nutrients and micronutrients, i.e. the ratio of particular nutrients to other nutrients, the ratio of particular nutrients to micronutrients, the ratio of particular micronutrients to particular micronutrients, or a combination of the above.

In addition, indirect markers can relate to the determination of functional markers in the diseased subject. Functional markers are markers relating to the status of physiological or biochemical parameters indicating the health status of a subject. For example, functional markers can be measurements such as erythrocyte transketolase activity, erythrocyte glutathione reductase activity, oxidative stress status, or nitric oxide synthase activity. These functional markers display a certain (reference) status in healthy subjects. In patients suffering from a disease, these markers may different values thus indicating inappropriate nutrient or micronutrient status relatively to healthy subjects. Appropriate provision of the diseased subject with appropriate set and levels of nutrients and micronutrients in a nutritional composition can be used to restore levels of these functional markers towards the levels measured in a healthy subject.

Samples:

The determination of the nutritional profile is performed on a sample derived from subjects.

The sample can be a sample selected from the group consisting of whole blood, blood plasma, blood serum, red blood cells, urine, or tissue biopsies. Depending on the determination method different samples will be obtained from the same subject. It is also possible to use a combination of samples from the same subject. It is also contemplated that a sample or a set of samples is obtained from a subject at a first time point and at a second or further time point an additional sample or set of samples is obtained. In this way, it is possible to measure changes of the nutritional profile in the subject over a time period.

Samples are processed according to technical requirements of subsequent analyses.

For instance, biological samples can be directly injected, after dilution, into the inductively coupled mass spectrometer for mineral and trace element analysis (elemental analysis including analysis of minerals). They can also be submitted to various steps of protein precipitation, extraction, clean-up, derivatization before being injected either on a gas liquid chromatographic system coupled to a flame ionization detector for fatty acid analysis or on a high pressure liquid chromatography coupled to mass spectrometry for the analysis of amino acids or hydrosoluble vitamins. Biological samples can also be processed to undergo colorimetric, fluorometric or immuno-assay analyses.

Nutritional profile and markers to be determined:

The nutritional profile encompasses direct and indirect markers. The markers can be biochemical, biological, or functional markers, or a combination thereof. Those markers are relevant for the nutritional status of a subject and thus indicate their nutritional requirements with respect to nutrients. These markers can be influenced by the nutrition consumed by the subject. These markers can be determined by the various methods described below.

The quantitative analysis of these markers indicate the nutritional requirements for nutrients. Nutrients can be macronutrients and micronutrients. Macronutrients can be protein, peptides, amino acids, fat, fatty acids, carbohydrates or choline. Micronutrients can be minerals, vitamins, carotenoids, phytonutrients. The nutrients can also be grouped by their function (functional nutrients), not depending on their structural similarities. For example, antioxidants provide an antioxidative effect, not dependent on their structure. Antioxidants can be vitamins, minerals, amino acids or peptides.

The status of at least 10, 25, 50, 100, 250 markers can be determined. There is no particular requirement for a maximum number of to be determined markers but an upper limit might be 25, 50, 100, 250, or 1000 markers.

Protein Markers:

Protein markers can be determined by markers of protein status or markers of protein catabolism and thus the nutritional requirements for nutrients providing protein or amino acids, or particular proteins and amino acids, can be determined. Protein status markers can be selected from the group consisting of albumin, pre-albumin, or/and phosphocreatine and combinations thereof. Markers of catabolism are selected from the group consisting of ammonia, urea, modified amino acids (monomethyl and dimethylarginine) or a combination thereof.

Amino Acid Markers:

Amino acid markers can be determined by determining the quantitation of amino acids or their derivatives, including their metabolites/catabolites, in a sample as an indication of their status and thus the nutritional requirements for nutrients providing protein or amino acids, or particular proteins and amino acids, can be determined.

Amino acid markers selected from the group consisting of alanine, β-alanine, sarcosine, arginine, monomethylarginine, assymetric-dimethylarginine, symmetric dimethylarginine, asparagine, aspartic acid, citrulline, glutamic acid, glutamine, glycine, histidine, 1-methylhistidine, 3-methylhistidine, isoleucine, leucine, lysine, methionine, ornithine, phenylalanine, proline, serine, taurine, threonine, tryptophan, tyrosine, valine, hydroxyproline, ethanolamine, α-aminobutyric acid, β-aminoisobutyric acid, γ-aminobutyric acid, homocysteine, cysteine, γ-glutamyl-cysteine, cysteinyl-glycine, homocystine, cysteine, cystathionine, methionine sulfoxid, selenomethionine, methionine sulfoximine, selenocysteine, selenocystine, ergothioneine, N-formyl-L-methionine, S-adenosylhomocysteine, S-Adenosylmethioninamine, alpha-ketobutyric acid, 2-aminobutyric acid, 2-amino-3-ketobutyric acid, alpha-keto-beta-methylbutyric acid (or alpha-ketoisovaleric acid), alpha-ketoisocaproic acid, or alpha-keto-beta-methylvaleric acid.

According to a preferred embodiment, the status of threonine, serine, or proline, preferably threonine, and thus the requirement thereof, is determined.

Figure 3:
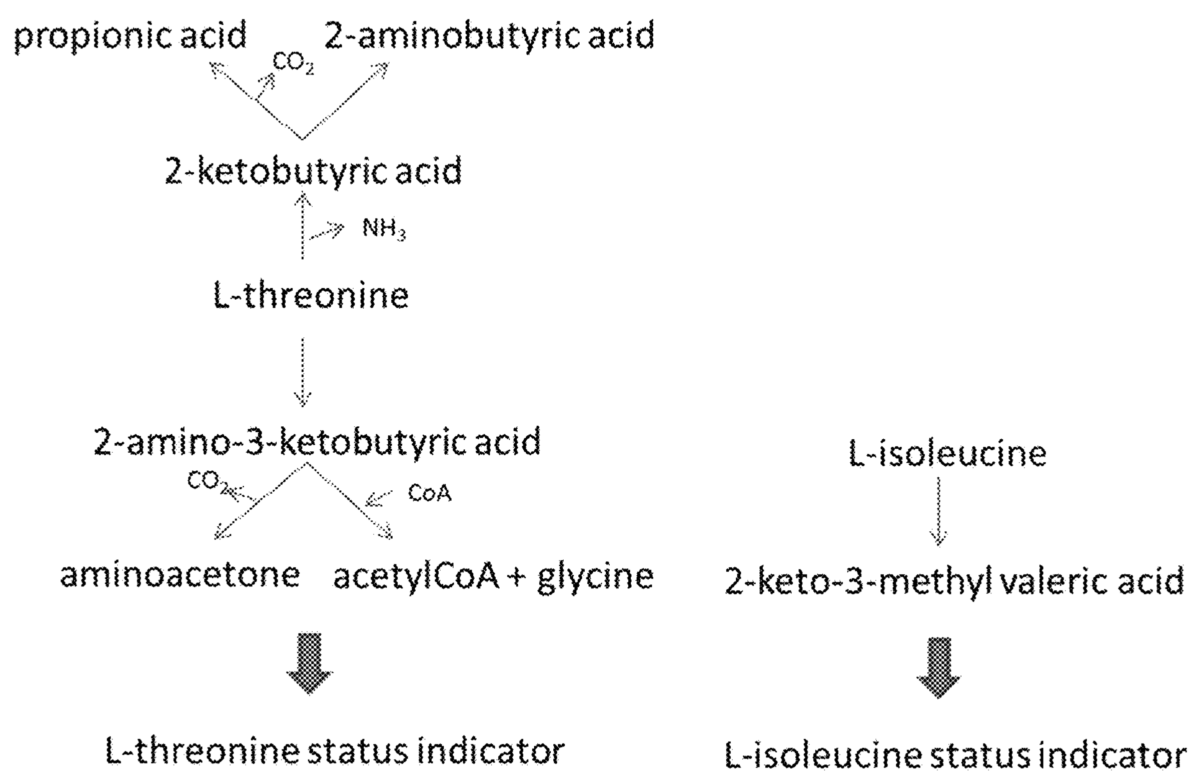
FIG. 3. Threonine and isoleucine metabolic products

Preferably, the indicator of the status of threonine is threonine and/or one catabolite or several catabolites of threonine. The catabolite(s) of threonine is(are) selected from the group consisting of propionic acid, 2-aminobutyric acid, 2-ketobutyric acid, 2-amino-3-ketobutyric acid, aminoacetone, acetylCoA, glycine, or a combination thereof (FIG. 3)

Preferably, the indicator of the status of isoleucine is isoleucine or a catabolite of isoleucine. The catabolite of isoleucine to be determined is preferably 2-keto-3-methyl valeric acid (FIG. 3).

Fatty Acid Markers:

Fatty acid markers can be determined by the quantitative analysis of fatty acids indicating their relative status and thus the nutritional requirements for nutrients providing fat, phospholipids (phosphatidylcholine, phosphatidylserine, phosphatidyletanolamine, etc.) or particular fatty acids can be determined.

Fatty acid markers selected from the group consisting of butyric C4:0, caproic C6:0, caprilic C8:0, capric C10:0, undecanoic 011:0, lauric C12:0, tridecanoic C13:0, myristic C14:0, pentadecanoic C15:0, palmitic C16:0, heptadecanoic C17:0, stearic C18:0, arachidic C20:0, heneicosanoic C21:0, behenic C22:0, lignoceric C24:0, myristoleic C14:1 n-5, cis-10-Pentadecenoic C15:1 n-5, palmitoleic C16:1 n-7, cis-10-heptadecenoic C17:1 n-7, elaidic C18:1 n-9 trans, oleic C18:1 n-9 cis, cis-11-Eicosenoic C20:1 n-9, erucic C22:1 n-9, nervonic 024:1 n-9, linoelaidic C18:2 n-6 trans, linoleic C18:2 n-6 cis, gamma-linolenic C18:3 n-6, alpha-Linolenic C18:3 n-3, cis-11,14-Eicosadienoic C20:2 n-6, cis-8,11,14-eicosatrienoic C20:3 n-6, cis-11,14,17-eicosatrienoic 20:3 n-3, arachidonic C20:4 n-6, cis-13,16-docosadienoic 22:2 n-6, cis-5,8,11,14,17-eicosapentanoic (EPA) C20:5 n-3, cis-4,7,10,13,16,19-Docosahexaenoic (DHA) C22:6 n-3 acid, or lipoic acid.

Element Markers (Including Mineral Markers):

Direct Element (including mineral) markers are measured in a sample either as their quantitation through elemental analysis and/or using the quantitation of their associated proteins or metabolites such as ferritin for iron status, ceruloplasmin for copper status, etc.

Element markers (including mineral markers) can be selected from the group consisting of lithium (Li), boron (B), magnesium (Mg), aluminium (Al), silicon (Si), phosphorous (P), sulfur (S), potassium (K), calcium (Ca), vanadium (V), chromium (Cr), manganese (Mn), iron (Fe), cobalt (Co), nickel (Ni), copper (Cu), zinc (Zn), arsenic (As), selenium (Se), bromine (Br), rubidium (Rb), strontium (Sr), molybdenum (Mo), tin (Sn), iodine (I), barium (Ba), titanium (Ti), sodium (Na), chlorine (Cl), fluorine (F).

Indirect element markers (including mineral markers) encompass combination of one or several elements and/or their associated proteins or metabolites.

Direct and indirect markers can be used to determine the dietary requirements for elements (including minerals).

Vitamin Markers:

Vitamin markers can be either direct or indirect markers. Direct markers encompass the quantification of vitamins and/or their metabolic products in a sample. Indirect markers encompass combination or one or several vitamins and/or their metabolic products as well as functional markers indicative of the status of vitamins such as for instance erythrocyte transketolase activity, erythrocyte glutathione reductase activity for the status of vitamin B1 (thiamine) and vitamin B2 (riboflavin), respectively.

Vitamin markers can be used to determine the dietary requirements for vitamins. The vitamins markers can be selected from the group consisting of hydrosoluble vitamins or liposoluble vitamins.

The hydrosoluble vitamins and their metabolites can be selected from the group consisting of vitamin B1 (thiamine), vitamin B2 (riboflavin), vitamin B3 (nicotinic acid or niacin), nicotinamide, methylnicotinamide, nicotinuric acid, choline, vitamin B5 (pantothenic acid), vitamin B6 (pyridoxine, pyridoxal, pyridoxamine), pyridoxal phosphate, pyridoxic acid, vitamin B8 (biotin), vitamin B9 (folic acid), methyl tetrahydrofolic acid, vitamin B12 (cyanocobalamin, methylcobalamin), hydroxycobalamin, adenosylcobalamin.

The liposoluble vitamins can be selected from the group consisting of vitamin A (retinol), vitamin K2 (menaquinone), vitamin K1 (phylloquinone), vitamin E (α-tocopherol, δ-tocopherol), vitamin D (25-OH vitamin D2, vitamin D25-OH D3, vitamin D2, vitamin D3, 1α-25-(OH)2 vitamin D3).

Nucleotide Markers:

Nucleotide markers and thus the requirements for nutrients providing nucleotides can be determined.

The nucleotides can be selected from the group consisting of inosine 5'monophosphate, adenosine 5'monophosphate, cytidine 5'monophosphate, guanosine 5'-monophosphate, inosine 5'monophosphate, uridine 5'monophosphate, or combinations thereof.

Phytonutrient Markers:

Phytonutrient markers and thus the requirements for nutrients providing phytonutrients can be determined.

In an embodiment the phytonutrients can be selected from the group consisting of carotenoids (e.g. lutein, zeaxanthin), ellagic acid, flavonoids (catechin, epicatechin, epigallocatechin), chlorogenic acids, resveratrol, glucosinolates, phytoestrogens (genistein, daidzein, etc.), or a combination thereof.

Peptide Markers:

Peptide markers and thus the requirements for nutrients providing peptides can be determined.

The peptides can be selected from the group consisting of reduced gluthathione or oxidized glutathione.

Oxidative Stress Markers:

Oxidative stress markers, and thus the requirements for nutrients improving oxidative stress status, can be determined.

In an embodiment the oxidative stress markers can be selected from the group consisting of 4-hydroxynonenal, malondialdehyde, nitrotyrosine, carbonylated proteins, total glutathione, reduced glutathione, oxidized glutathione, glutathione peroxidase activity, glutathione reductase activity, superoxide dismutase activity, catalase activity, or a combination thereof.

Nutrients affecting the oxidative stress status can be dietary oxidants. The dietary oxidants can be vitamins, minerals (e.g. selenium), phytochemicals, amino acids (e.g. cysteine) or peptides (e.g. glutathione). These nutrients reestablish oxidative stress level similar to the one of healthy subject.

Nitric Oxide Synthase Activity: Markers of nitric synthase activity and thus the requirements for nutrients affecting nitric oxide synthase activity can be determined.

In an embodiment, markers of nitric synthase activity can be selected from the group consisting of nitrite, nitrate, monomethyl arginine, asymmetric dimethylarginine, symmetric dimethylarginine, arginine, citrulline, ornithine, argininosuccinic acid or a combination thereof.

Osmolyte Markers:

Markers for osmolytes and thus the requirements for nutrients affecting osmolyte status can be determined. These markers are functional markers.

In an embodiment, the osmolyte markers can be selected from the group consisting of trimethylamine N-oxide, dimethylsulfoniopropionate, trimethylglycine, sarcosine, betaine, glycerophosphorylcholine, myo-inositol, or a combination thereof.

Methods for Quantifying Markers:

Various methods are known for determining the above described markers of nutritional status in a sample. Non-limiting examples of various methods of how to perform a quantification of said markers, are described below. Other suitable methods known in the art may additionally/alternately be used.

The nutritional status of a subject in the sense of the invention relates to a profile of the status of direct or indirect markers, that can indicate the status of nutrients and micronutrients, which can be biochemical, biological, functional, or other markers.

Direct biochemical markers can be the concentration of particular nutrients. Nutrients can be macronutrients (e.g. proteins and derived amino acids, carbohydrates, lipids) or micronutrients (vitamins and elements (including minerals)).

An indirect biochemical marker can be a nutrient status indicator that either relates to macronutrients or micronutrients, or a combination thereof.

A nutrient status indicator can be a biomarker whose concentration indicates the status of a nutrient without being said nutrient itself. For example, ferritin for iron or 25-hydroxy-vitamin D vitamers for vitamin D.

Other nutrient status markers can be derived from concentrations of single nutrients or its metabolites or combination of concentrations from nutrients and their metabolites (ratios) or combination of concentrations of nutrients with other biochemical markers (e.g. transport protein for nutrients/micronutrients) and/or biological and/or functional markers (e.g. specific enzymatic activity such as transketolase activity, erythrocyte glutathione reductase activity).

Various methods exist to determine the status of direct or indirect biochemical markers. In the following we will discuss various quantification methods for said markers. However, it should be understood that the respective method of quantification is not decisive for the method of the invention as long as it outputs the nutritional requirement for a particular nutrient or set of nutrients.

Indicator of Amino Acid Oxidation (IAAO) Methodology:

As an example, the specific requirement for an essential amino acid can be quantified using the indicator of amino acid oxidation (IAAO) methodology (Roberts S A, Thorpe J M, Ball R O, Pencharz P B.; Am J Clin Nutr. 2001 February, 73(2):276-82.; Elango R, Ball R O, Pencharz P B., J Nutr. 2008 February; 138(2):243-6. Review). Because of the limitations with N-balance the stable isotope carbon oxidation based methods have been developed to evaluate essential amino acid requirements in humans (Pencharz P B, Ball R O. *Different approaches to define individual amino acid requirements*. Annu Rev Nutr. 2003; 23:101-16.). The IAAO method has been validated for estimating amino acid requirements with minimal prior adaptation (Bross R, Ball R O, Pencharz P B., J Nutr. 1998 November; 128(11):1913-9; Thorpe J M, Roberts S A, Ball R O, Pencharz P B., J Nutr. 1999 February; 129(2):343-8.). The IAAO technique is based on the concept that when one essential amino acid is deficient for protein synthesis, then all other amino acids including the so-called indicator amino acid (usually L-[1-$^{13}$C]phenylalanine) are in excess since less used, and therefore will be oxidized (Pencharz and Ball 2003). This is primarily because excess amino acids cannot be stored and therefore must be partitioned between incorporation into protein or oxidation. With increasing intake of the limiting amino acid, oxidation of the indicator amino acid will decrease, reflecting increasing incorporation into protein. Once the requirement is met for the limiting amino acid, there will be no further change in the oxidation of the indicator amino acid with increasing intake of the test amino acid. The inflection point where the oxidation of the indicator amino acid stops decreasing and reaches a plateau is referred to as the 'breakpoint'. The breakpoint, identified with the use of bi-phase linear regression analysis, indicates the estimated average requirement of the limiting (test) amino acid. A particular strength of the IAAO model is that the absolute level of oxidation does not matter, rather the relative oxidation across the broad range of intake levels result in the same break-point (requirement estimate). This method is a well-accepted approach but it presents major limitations. Indeed it can only be applied to essential amino acids, it allows the assessment of only one essential amino acid per clinical study, it is invasive for the patient (kinetic studies of tracers and several time-points with different diets), and it is time consuming.

Nutritional Profile (or Nutrient Profiling):

Nutrient requirements can be determined using the quantitative analysis of nutrients and their metabolic products, i.e. referred as nutrient profiling, in biological samples. Nutrient profiling is achieved using a combination of analytical methods based on analytical techniques such as high performance liquid chromatography, gas chromatography, mass spectrometry, spectrophotometry or immuno assays. Nutrient profiling encompasses concentration determination of a broad range of nutrients and micronutrients and their metabolic products (metabolites) as well as relative protein nutrient/micronutrient transporters, or functional biomarkers such as nutrient/micronutrient specific enzymatic activities. This nutrient profiling approach has the advantage to cover a comprehensive range of nutrients and micronutrients, enabling thus the possibility to assess nutrient-nutrient interactions, as well as to be faster and relatively less invasive for the patients as no kinetic studies are needed.

Related to the determination of amino acid requirements, the concomitant analysis of concentrations of amino acids and their specific metabolic products can be used to determine specific amino acid oxidation. The measurement of oxidation of specific amino acids, as a result of protein oxidation, can be used to infer their relative incorporation into proteins and therefore their specific requirements to meet the metabolic demand for protein synthesis. For instance, threonine is oxidized into 2-keto butyric acid 2-aminobutyric acid, and 2-amino-3-ketobutyric acid (FIG. 3).

As an example, the concomitant analysis of the concentrations of threonine and its metabolites can be used to assess threonine oxidation (see FIG. 3, left side). The threonine oxidation is then compared to the one from another essential amino acid, taken as benchmark, such as for instance isoleucine (see FIG. 3, right side). In the case of isoleucine, the oxidation is measured using determination of concentrations of isoleucine and its oxidation product, 2-keto 3-methylvaleric acid (see FIG. 2, right side). Oxidation is defined as the calculated product of the combination of concentrations of threonine and its metabolite(s), such as:

- Ratio concentration of L-threonine/concentration of 2-keto butyric acid
- Ratio concentration of L-threonine/(concentration of 2-keto butyric acid+concentration of 2-aminobutyric acid)
- Ratio concentration of L-threonine/(concentration of 2-keto butyric acid+concentration of 2-aminobutyric acid+concentration of 2-amino 3-ketobutyric acid)
- or any mathematical combination of thereof
- or any mathematical combination of thereof and other markers or product of protein catabolism such as concentration of circulating ammonia, intermediates in urea cycle (ornithine, citrulline, arginine succinic acid, arginine), concentrations of symmetric dimethylarginine, asymmetric dimethylarginine.
- Any combination of thereof and markers of oxidative stress, nitric oxide metabolism (nitric oxide levels in blood plasma/serum, nitrate levels in urine).
- Any combination of thereof and clinical markers used to monitor, for example, IBD activity: CRP, differential blood count, fecal calprotectin, iron status, blood sedimentation rate, protein electrophoresis, fecal neutrophils, vitamin B12 status, and others.

For example, the oxidation of threonine and isoleucine can be compared between a diseased and a healthy subject as has been done in FIG. 4 (here the example relates to IBD as the disease of interest). As can been seen from FIG. 4 only in the case where the threonine oxidation is lower compared to the healthy subject an enhanced nutritional requirement for threonine in IBD can be identified.

As such the invention also relates to a method for determining the nutritional requirements for threonine and/or isoleucine comprising comparing the oxidation of threonine and/or isoleucine of diseased and a healthy subject.

Amino acid quantification with Ultra Performance Liquid Chromatography coupled to tandem mass spectrometry:

Amino acids can be also directly measured in a sample obtained from the subject.

Sample Preparation

50 μL of blood plasma or serum is added with 10 μL labelled internal standards and 140 μL of cold methanol (0.1% formic acid) for protein precipitation. Samples then undergo agitation with vortex (5 min) followed by centrifugation at 10000 rpm for 10 min at 4° C. Supernatant is then collected to undergo derivatization.

Amino Acid Derivatization

Derivatization is performed using the AccQ-Tag Ultra Derivatization Kit Amino Acid Analysis (Waters Corp.) following manufacturer's procedures: 10 μL of either a standard amino acid mix solution or the supernatant of the sample is mixed with 70 μL of AccQ-Tag Ultra borate buffer (pH=8.8). The derivatization is carried out by adding 20 μL of reconstituted AccQ-Tag Ultra reagent (3 mg/mL of 6-aminoquinolyl-N-hydroxysuccinimidyl carbamate, or AQC in acetonitrile) to the buffered mixture. The sample is then immediately vortexed followed by incubation for 15 min at 55° C.

Analysis of Amino Acids Using Ultra Performance Liquid Chromatography Coupled to Tandem Mass Spectrometry (UPLC-MS/MS)

UPLC-MS/MS analysis is performed on a Waters Acquity UPLC system on-line coupled to a Waters Xevo TQ mass spectrometer by means of an electrospray ionization (ESI) probe. Chromatographic separation is achieved using a Waters AccQ-Tag Ultra column (2.1 mm i.d.×100 mm, 1.7 μm particles) using a binary system of eluents A and B. Eluent A contains 10% of commercial solution of AccQ-Tag Ultra Eluent A concentrate (Waters Corp.) in 90% water. Eluent B is a commercial solution of AccQ-Tag Ultra Eluent B (Waters Corp.). The separation gradient used is: 0-0.54 min (99.9% A), 5.74 min (90.9% A), 7.74 min (78.8% A), 8.04 (40.4% A), 8.05-8.64 (10% A), 8.73-10.0 (99.9% A). The autosampler temperature is set at 20° C. and the column temperature at 55° C. The sample injection volume is 2 μL. Cone voltage and collision energy values are determined on each measured amino acid using the Waters IntelliStart routine. The ion m/z 171 representing the common main product from the collision-induced dissociation of all the AQC adducts, was used for the quantification of individual amino acids. Retention times of amino acids are determined using injection of standard amino acid solutions into the UPLC-ESI-MS/MS system. The following ionization source settings were used: capillary voltage, 2.5 kV (ESI+); desolvation temperature, 600° C.; desolvation gas flow rate, 1000 L/h; source temperature, 150° C.

The analyzer settings are determined during each calibration periods with typical values as following: first quadrupole 2.95 (low mass resolution), 14.35 (high mass resolution), ion energy 1:0.1; second quadrupole 2.95 (low mass resolution) and 14.40 (high mass resolution), ion energy 2:0.3. Argon was used as collision gas at a flow rate of 0.15 $mL \cdot min^{-1}$. The UPLC-MS/MS system control and data acquisition were performed with the Waters Corporation MassLynx™ software. Data analysis was conducted with the TargetLynx™ software (Waters Corporation).

Quantification of Fatty Acids by Gas-Liquid Chromatography:

The concentration of fatty acids can be determined with any suitable method like thin layer chromatograph or gas chromatography.

In the following we will exemplify a gas chromatography method.

Sample Preparation

Derivatization of plasma and red blood cell (RBC) fatty acids are performed under acidic conditions. Briefly, 200 μL of sample are mixed with methanol, methanolic hydrochloric acid, hexane and internal standard solution in screw-capped glass tubes. The tubes are capped and heated at 100° C. for 60 min for plasma and 90 min for RBC followed by a cooling phase to room temperature and an addition of water to stop the reaction. Then the tubes are centrifuged at 1200 g for 5 min and the upper organic phase is collected and analyzed by gas chromatography (GC).

Fast Analysis of Fatty Acid Methyl Esters (FAMEs) by Gas-Liquid Chromatography

Analysis of total FAM Es is performed on a 7890 Agilent gas chromatograph (Agilent Technologies, Palo Alto, Calif., USA), equipped with a fused-silica BPX-70 capillary column (10 m×0.1 mm I.D., 0.2 m film thickness; SGE, Melbourne, Australia). Split injector (35:1) and flame-ionization detection (FID) system were operating at 250° C. and 300° C. respectively. The volume of the oven has been reduced to about 5400 $cm^3$ using a commercial device obtained from Agilent. Oven temperature programming was 45° C. isothermal for 0.5 min, increased to 180° C. at 100° C./min, isothermal for 0.5 min at this temperature then increased to 220° C. at 9° C./min, isothermal for 0.5 min at this temperature and then to 250° C. at 50° C./min (total run time 7.9 min). The carrier gas ($H_2$) flow was maintained constant at 0.7 $mL \cdot min^{-1}$ and the acquisition of the FID signal at 50 Hz.

Identification of FAMEs

A mixture of standard FAM Es is used to confirm identification of fatty acids. The mixture contains methyl esters of: butyric acid (4:0), caproic acid (6:0), caprylic acid (8:0), capric acid (10:0), undecanoic acid (11:0), lauric acid (12:0), tridecanoic acid (13:0), myristic acid (14:0), myristoleic acid (14:1 n-5), pentadecanoic acid (15:0), pentadecenoic acid (15:1 n-5), palmitic acid (16:0), palmitoleic acid (16:1 n-7), heptadecanoic acid (17:0), heptadecenoic acid (17:1 n-7), stearic acid (18:0), elaidic acid (trans-18:1 n-9), oleic acid (18:1 n-9), linolelaidic acid (all trans-18:2 n-6), linoleic acid (18:2 n-6), arachidic acid (20:0), γ-linoleic acid (18:3 n-6), eicosenoic acid (20:1 n-9), linolenic acid (18:3 n-3), heneicosanoic acid (21:0), eicosadienoic acid (20:2 n-6), behenic acid (22:0), eicosatrienoic acid (20:3 n-6), erucic acid (22:1 n-9), eicosatrienoic acid (20:3 n-3), arachidonic acid (20:4 n-6), docosadienoic acid (22:2 n-6), lignoceric acid (24:0), eicosapentanoic acid (20:5 n-3), nervonic acid (24:1 n-9) and docosahexaenoic acid (22:6 n-3).

Quantification of Sulfur Containing Molecules:

Sulfur containing molecules encompass amino acids and derivates (homocysteine, cysteine, γ-glutamyl-cysteine, cysteinyl-glycine, homocystine, cysteine, cystathionine, methionine sulfoxid, selenomethionine, methionine sulfoximine, selenocysteine, selenocystine, ergothioneine, N-formyl-L-methionine, S-adenosylhomocysteine, S-Adenosyl methioninamine), peptides (reduced gluthatione and oxidized gluthatione), and lipoic acid.

Sample Preparation

Blood plasma, serum or red blood cell samples (50 μl) are mixed with 50 μl of internal standard glutathione ethyl ester (GSHee) before being treated with 100 μl of derivatization solution containing 10 mM lodoacetic acid in 10 mM aqueous ammonium bicarbonate and ammoniac (0.5% v/v, pH 9.5). This mixture is stored at room temperature for 15 minutes. The reaction is stopped and the proteins are precipitated by addition of 50 μl of cold sulfosalicylic acid solution (10% w/v). The mixture is then centriguged at 16000×g at 4° C. for 15 minutes. The supernatant (200 μl) is transferred to glass vials and 2 μl were injected into the Analysis of Derivatized Sulfur Containing Molecules Using Ultra Performance Liquid Chromatography Coupled to Tandem Mass Spectrometry (UPLC-MS/MS)

UPLC-MS/MS analysis is performed on a Waters Acquity UPLC system on-line coupled to a Waters Xevo TQ mass spectrometer by means of an electrospray ionization (ESI) probe. Chromatographic separation is achieved using a Waters HSS T3 2.1 mm+100 mm, 1.7 μm column. Elution is performed at a flow rate of 0.25 mL/min using a gradient composed of solvents A (0.1% formic acid in water) and B (acetonitrile/water 20:80, v/v with 0.1% formic acid). The gradient was as follows: 100% solvent A 0-2 min, 1% solvent A 2-7 min, 99% solvent A 7.1-10 min. The mass spectrometer operates under the following conditions: capillary voltage: 2.5 KV; source temperature: 150° C.; desolvation temperature: 600° C.; desolvation gas flow: 1000 L/Hr. For quadrupole 1, the low and high mass resolution are 2.95 and 14.35, respectively, with a ion energy of 0.1. For the quadrupole 2, the low and high mass resolution are 2.95 and 14.40, respectively, with a ion energy of 0.3. Argon is used as collision gas at a flow rate of 0.15 mL/min. MRM transitions with their respectively optimized cone voltage and collision energy values were determined for each metabolite using the Waters IntelliStart software. Using these conditions, each sulfur containing molecules is injected into the UPLC-MS/MS system to determine the retention time. The MRM-MS method is built to monitor only one transition channel per MRM function. The UPLC-ESI-MS/MS system control and data acquisition were performed with the Waters Corporation MassLynx™ software. Data analysis was conducted with the TargetLynx™ software (Waters Corporation).

Quantification of Elements (Including Minerals):

Elements (including minerals) can be quantified by any suitable method known in the art. An example is provided in the following.

Sample Preparation

A volume 150 μL of biological fluid (blood plasma, serum, urine, etc.) is diluted 1:10 in a diluent solution containing 5% 1-butanol, 0.05% EDTA, 0.05% Trition X-100, and 1% ammonium hydroxid.

Elemental Analysis Using Inductively Coupled Plasma Triple Quadrupole Mass Spectrometry (ICP-MS/MS)

Elemental analysis is performed using a 8800 ICP-MS/MS spectrometer (Agilent Technologies, Tokyo, Japan) that is operated in low matrix plasma mode. The ICP-MS system is equipped with an integrated auto sampler for direct sample introduction. The samples are pumped at a flow rate of 0.35 $mL\ min^{-1}$ through an integrated peristaltic pump into the sample introduction area, consisting of a concentric nebulizer and a Scott double-pass spray chamber. After ionization in the plasma, the analyte-ions are transferred into the mass spectrometer. The ICP-MS system is equipped with a triple-quadrupole mass analyzer which allows applying MS/MS analysis mode. Quantification of each mineral is achieved by external calibration. In order to correct or reduce plasma fluctuations and matrix effects, on-line dilution is applied to mix the samples with a multi-element internal standard solution. For quality control, a human certified reference material (Seronorm Trace Elements Serum L-1 from Sero, Norway) is analysed during each analytical run. The measured elements are listed on Appendix 1.

Element Speciation Analysis Using High Performance Liquid Chromatography Coupled to Inductively Coupled Plasma Triple Quadrupole Mass Spectrometry (UHPLC-ICP-MS/MS)

For all chromatographic experiments, a 1290 Infinity dual-piston UHPLC pump (Agilent Technologies, Tokio, Japan) is used. Analysis of mineral species, weakly associated to biomolecules, is achieved by size exclusion chromatography coupled to ICP-MS, applying 50 mM ammonium acetate (pH 7.4) as mobile phase in isocratic elution mode. For the analysis of stable species, reversed phase (RP) HPLC-ICP-MS is used, applying gradient elution at a flow rate of 0.4 mL $min^{-1}$. Mobile phase A is composed of 2% acetonitrile (ACN), 0.05% TFA (trifluoroacetic acid) and mobile phase B of 98% ACN, 0.05% TFA. A typical gradient consists of a linear increase of acetonitrile from 5% to 80% within 30 min. For analysis of biological fluids an injection volume of 3-20 μL is applied. Identification of the mineral species is achieved by collecting fractions corresponding to the detected chromatographic peaks. Finally, the collected fractions were preconcentrated, desalted and analysed by molecular MS for identification of the biomolecules. Quantification is achieved by post-column isotope dilution analysis. Here, the isotopically enriched elements are dissolved in 2% nitric acid and injected by a peristaltic pump, maintaining a constant flow rate of 0.2 mL $min^{-1}$.

Hydrosoluble Vitamins:

Hydrosoluble vitamins can be directly quantified in a sample obtained from the subject.

Chemicals

Vitamin standards, formic acid, acetic acid are purchased from Sigma-Aldrich (St. Louis, Mo.), Millipore water were from Water (Milford, Mass.), acetonitrile was purchased from VWR (Radnor, Pa.). Labelled vitamin standards are purchased from Cambridge Isotope Laboratories (Tewksbury, Mass.).

Sample Preparation

Plasma/serum was stored at −80° C. unfrozen and immediately put on ice. Plasma/serum is spiked with labeled internal standards mixed and kept for 10 min. Proteins are precipitated by mixing 100 μl of plasma/serum with 100 μl of 10% TCA acid. Samples are extracted for 10 min on ice and centrifuged at 4° C. for 10 min at 17000 rpm for the analysis of B1, B2, B3, B6, B7 vitamins and metabolites. 100 μl of serum/plasma is mixed with 200 μl 90% methanol/water solution containing acetic and ascorbic acids for the analysis of vitamin B9. Samples are stirred for 20 min, centrifuged and supernatant was dried down under nitrogen stream. Samples were re-suspended with water and injected using described earlier UPLC conditions.

Analysis of B1, B2, B3, B6, B7 and B9 Vitamins and Metabolites Using Ultra Performance Liquid Chromatography coupled to tandem mass spectrometry (UPLC-MS/MS)

10 μl of supernatant is injected into a Waters Acquity UPLC system on-line coupled to a Waters Xevo TQ mass spectrometer by means of electrospray ionization (ESI) probe. Chromatographic separation is achieved using a Waters Acquity UPLC® HSS T3 2.1×100 mm column, 0.6 ml flow rate, solvent A—0.1% formic acid in water, solvent B—0.1% formic acid in acetonitrile. Gradient program from 100% of A to 100% of B within 9 min. Detection of vitamins was performed on Waters XEVO TQS mass spectrometer in scheduled MRM mode with 2 transitions per vitamin. The UPLC-MS/MS system control and data acquisition were performed with the Waters Corporation MassLynx™ software. Data analysis was conducted with the TargetLynx™ software (Waters Corporation).

Liposoluble Vitamins:

Liposoluble vitamins can be directly quantified in a sample obtained from the subject.

Chemicals

Hexane, methanol, ethanol, deionized water and acetonitrile are purchased from VWR (Radnor, PE) international. Standards of vitamins are purchased from Sigma Aldrich (St. Louis, Mo.). Analytical column (HSS C18, 1.7□m 3×100 mm) and solid-phase extraction (SPE) plats are purchased from Waters (Milford, Mass.).

Sample Preparation

In order to protect vitamins from light degradation, the sample preparation steps are performed under ultraviolet (UV) protection by means of filters properly implemented in the laboratory.

Liposoluble vitamins are extracted using a protein precipitation combined with a liquid-liquid extraction procedure. Briefly, 200 □l of a solution of butylated hydroxyl toluene (BHT) in ethanol are added to 200 □l of human serum to perform protein precipitation and sample preservation from oxidation. Samples are then extracted with 2.5 ml of n-hexane, sonicated and centrifuged for three times. The collected supernatants are combined and dried under nitrogen flow to be finally reconstituted in n-hexane/isopropanol 9:1.

The two 25-hydroxyvitaminD metabolites undergo a different extraction protocol. Briefly, 150 □l of human serum are added with using 150□□l of methanol) for protein precipitation. Supernatant fractions collected by centrifugation (15 min at 4 C° 4000 rpm) are collected and submitted to SPE clean-up step using Oasis HLB (Waters, Milford, Mass., USA) cartridges preconditioned with methanol and water. Cartridges are loaded with samples and washed with water and 5% methanol solution. The elution of the analyses is obtained using methanol. The samples are then dried and reconstitute in n-hexane/isopropanol 9:1.

Analysis of Liposoluble Vitamins and Metabolites Ultra-Performance Convergence Chromatography to Tandem Mass Spectrometry ($UPC^2$-MS/MS)

$UPC^2$-MS/MS analysis is performed on a Waters Acquity Ultra-Performance Convergence Chromatography ($UPC^2$) system equipped with Xevo TQS mass spectrometer (Waters Corporation). An HSS C18 analytical column is utilized to perform the chromatographic separation and it connected with pumps: A (mobile phase, CO2) and Pump B (mobile phase, 10 mM ammonium acetate Methanol solution). The gradient applied starts from 2% of organic solvent until 40% in a total run time of 14 minutes using 1.2 ml flow rate. The MS analysis are as follows: capillary voltage: 2.6 kV, desolvation temperature: 500° C., cone gas flow rate: 150 L/hr, desolvation gas flow rate: 500 L/hr. The multiple reaction monitoring (MRM) is applied to perform this analysis. The UPLC-MS/MS system control and data acquisition were performed with the Waters Corporation MassLynx™ software. Data analysis was conducted with the TargetLynx™ software (Waters Corporation).

For example, the amount of 25-hydroxy-vitamin D vitamins can be used to determine the status of vitamin D.

Further Micronutrient Analyses:

Vitamin or mineral/trace element status can be performed using the exemplary methods described below.

Vitamin B12 and vitamin B9 (folate) status can be measured using the competitive principle.

The quantification of plasma/serum methylmalonic acid and total homocysteine, as well as plasma concentration of holotranscobalamin II can be performed for vitamin B12 status.

The quantification of ferritin, soluble transferrin transporter, or hepcidin can be performed for iron status.

The quantification of tyroxine T4 and T3 can be performed for iodine status.

The quantification of ceruloplasmin and copper/zinc superoxide dismutase can be performed for copper status.

Further Analyses of Metabolites:

Additional analyses are performed on blood plasma/serum for ammonia and urea quantitation using a Cobas® C111 (Roche Diagnostics). Measured are performed by spectrophotometry. Ammonia concentration is calculated endpoint decrease at 340 nm (wavelength A) and 629 nm (wavelength B). Urea concentration is determined using a calculation mode by kinetic decrease at 340 nm (wavelength A) and 409 nm (wavelength B).

Compositions:

The compositions of the invention comprise nutrients in an amount that reestablish in the diseased person the metabolic, physiologic and functional equivalence of the nutritional profile or status of a healthy person or healthy cohort.

First, the distinctive nutritional requirements of the diseased person or a cohort of diseased patients with the same disease or the same severity grade of the disease are determined.

In this way, nutrients can be identified that are not provided in optimal amounts to the diseased patient, thus are provided in a too low or too high amount, generally in a too low amount.

Nutritional compositions can then be adapted to contain the nutrients in an amount that will recover the nutritional profile of the diseased person towards the nutritional profile of a healthy person. Optimally, the nutritional profile of the diseased subject will have the same or almost identical nutritional status after consumption of the nutritional composition adapted to the diseased subject.

For example, a nutritional composition for a diseased subject exhibiting a deficiency in threonine as determined by the IAAO methodology contains threonine either in the form of free threonine or/and protein bound threonine in an amount that will reduce or eliminate the threonine deficiency.

Accordingly, the nutritional composition can either be a supplement comprising only those nutrients that are underrepresented in a regular diet.

Alternatively, the nutritional composition can be in the form of a complete food providing all the nutrients that the diseased person requires for normal nutritional status, and thus both nutrients for which the subject has distinctive nutritional requirements compared to a healthy subject and those nutrients for which the subject has the same nutritional requirements as a healthy subject. A complete food might contain those nutrients in a less amount for which the diseased person has a reduced requirement compared to a healthy subject.

Formulations:

The above described compositions can be formulated in liquid or solid form.

The compositions can further comprise at least one additional active agent, carrier, vehicle, excipient, or auxiliary agent identifiable by a person skilled in the art upon reading of the present disclosure.

The composition can be in the form of an a nutritional composition or pharmaceutical product. A nutritional composition or pharmaceutical product can comprise the composition of the invention.

Nutritional Composition:

As used herein, the term "nutritional composition" includes, but is not limited to, complete nutritional compositions, partial or incomplete nutritional compositions, and disease or condition specific nutritional compositions. A complete nutritional composition (i.e., those which contain all the required essential macro and micro nutrients) can be used as a sole source of nutrition for the patient. Patients can receive 100% of their nutritional requirements from such complete nutritional composition. A partial or incomplete nutritional composition does not contain all the essential macro and micro nutrients and cannot be used as a sole source of nutrition for the patient. Partial or incomplete nutritional compositions can be used as a nutritional supplement, i.e. in addition to a patient's diet. An oral supplemental nutritional composition contains those nutrients for which the diseased person has an increased demand compared to a healthy person as identified with the method of the invention.

A complete nutritional composition typically has an energy density of having a caloric density of 0.7-2.0 kcal/ml (2.9-8.4 kJ/ml).

A nutritional composition may comprise the following macronutrients and micronutrients: a source of proteins, a source of lipids, a source of carbohydrates, vitamins and elements (including minerals).

The source of protein can be animal, milk, or plant protein.

The nutritional composition further includes one or more free amino acids. Non-limiting examples of amino acids include alanine, arginine, asparagine, aspartate, citrulline, cysteine, glutamate, glutamine, glycine, histidine, hydroxyproline, hydroxyserine, hydroxytyrosine, hydroxylysine, isoleucine, leucine, lysine, methionine, phenylalanine, proline, serine, taurine, threonine, tryptophan, tyrosine, valine. Examples for non protein amino acids are citrulline, HICA (Alpha-Hydroxyisocaproic Acid), HIVA (Alpha-Hydroxyisovaleric Acid), HIMVA (alpha-hydroxymethylvaleric acid) or a combination thereof.

Free amino acids can be the only source of protein in the composition or combined with other sources of protein. Each amino acid is present in an amount of 0.5%-25% of the total amino acids.

The source of fat may either be an animal fat or a vegetable fat or both. Although animal fats have essentially equal caloric and nutritional values and can be used interchangeably, vegetable oils are preferred in the practice of the present invention due to their readily availability, ease of formulation, and lower concentration of saturated fatty acids. Fat sources to be used comprise fish oil, egg oil, algal oil, corn oil, sunflower oil, safflower oil, canola oil, coconut oil and/or soybean oil or combinations thereof.

The nutritional composition may comprise elements and minerals such as boron, calcium, calcium acetate, calcium gluconate, calcium chloride, calcium lactate, calcium phosphate, calcium sulfate, chloride, chromium, chromium chloride, chromium picolonate, copper, copper sulfate, copper gluconate, cupric sulfate, fluoride, iron, carbonyl iron, ferric iron, ferrous fumarate, ferric orthophosphate, iron trituration, polysaccharide iron, iodide, iodine, magnesium, magnesium carbonate, magnesium hydroxide, magnesium oxide, magnesium stearate, magnesium sulfate, manganese, molybdenum, phosphorus, potassium, potassium phosphate, potassium iodide, potassium chloride, potassium acetate, selenium, sulfur, sodium, docusate sodium, sodium chloride, sodium selenate, sodium molybdate, zinc, zinc oxide, zinc sulfate and mixtures thereof. Non-limiting exemplary derivatives of mineral compounds include salts, alkaline salts, esters and chelates of any mineral compound cited above.

The nutritional composition may further comprise vitamins such as vitamin B1 (thiamin, thiamin pyrophosphate, TPP, thiamin triphosphate, TTP, thiamin hydrochloride, thiamin mononitrate), vitamin B2 (riboflavin, flavin mononucleotide, FMN, flavin adenine dinucleotide, FAD, lactoflavin, ovoflavin), vitamin B3 (niacin, nicotinic acid, nicotinamide, niacinamide, nicotinamide adenine dinucleotide, NAD, nicotinic acid mononucleotide, NicMN, pyridine-3-carboxylic acid), vitamin B3-precursor tryptophan, vitamin B6 (pyridoxine, pyridoxal, pyridoxamine, pyridoxine hydrochloride), pantothenic acid (pantothenate, panthenol), folate (folic acid, folacin, pteroylglutamic acid), vitamin B12 (cobalamin, methylcobalamin, deoxyadenosylcobalamin, cyanocobalamin, hydroxycobalamin, adenosylcobalamin), biotin, vitamin C (ascorbic acid), vitamin A (retinol, retinyl acetate, retinyl palmitate, retinyl esters with other long-chain fatty acids, retinal, retinoic acid, retinol esters), vitamin D (calciferol, cholecalciferol, vitamin D3, 1,25,-dihydroxyvitamin D), vitamin E (a-tocopherol, a-tocopherol acetate, a-tocopherol succinate, a-tocopherol nicotinate, a-tocopherol), vitamin K (vitamin K1, phylloquinone, naphthoquinone, vitamin K2, menaquinone-7, vitamin K3, menaquinone-4, menadione, menaquinone-8, menaquinone-8H, menaquinone-9, menaquinone-9H, menaquinone-10, menaquinone-11, menaquinone-12, menaquinone-13), choline, inositol, 6-carotene and any combinations thereof.

A complete nutritional composition typically comprises 10-40 en % protein, 10-60 en % carbohydrates, and 20-80 en % fat. "en %" is the amount of energy provided to the total of the energy of the nutritional composition.

The composition may also contain anti-oxidants, stabilizers (when provided in solid form) or emulsifiers (when provided in liquid form).

Format of the Nutritional Composition:

In one embodiment, the nutritional composition is selected from the group consisting of supplemental nutritional composition, a complete nutritional composition, a yoghurt product, fermented milk, a fruit juice, a dried powder in sachet format or a cereal bar.

The nutritional composition may be a medical food, also referred to as a food for special medical proposes. A medical food product is specially formulated and intended for the dietary management of diseases or medical conditions (e.g., prevent or treat diseases or undesirable medical conditions). A medical food product can provide clinical nutrition, for example fulfilling special nutritional needs of patients with a medical condition or other persons with specific nutritional needs.

The medical food may be in the form of a health care nutritional composition for oral feeding, and/or a nutritional product for enteral or parental feeding. In the case of a product for parenteral feeding it will only include ingredients which are suitable for parenteral feeding. Ingredients that are suitable for parental feeding are known to the person skilled in the art.

In an embodiment, the medical food can be in the form of a nutritionally complete product, a drink, a dietary supplement, a meal replacement, a food additive, a supplement to a food product, a powder for dissolution, an enteral nutrition product, an infant formula, and combinations thereof.

In an embodiment, the nutritional composition may be in the form of a fermented milk, a yogurt, a fresh cheese, a renneted milk, a confectionery bar, breakfast cereal flakes, a breakfast cereal bar, a drink, a milk powder, a soy-based product, a non-milk fermented product, or a nutritional supplement for clinical nutrition. In an embodiment the composition may be in the form of a powder, in particular a powder for reconstitution with a liquid. In an embodiment the composition may be in the form of a liquid, for example a ready-to-drink liquid oral nutritional supplement.

In an embodiment, the nutritional compositions are in a form selected from the group consisting of tablets, capsules, liquids, chewables, soft gels, sachets, powders, syrups, liquid suspensions, emulsions, solutions, or combinations thereof. In an embodiment, the nutritional compositions are oral nutritional supplements. Alternatively, the nutritional compositions may be tube feedings.

Viscosity:

If the nutritional composition is a liquid it has a viscosity below 150 mPa·s, preferably below 100 mPa·s, more preferably below 80 mPa·s, even more preferably below 70 mPa·s. The viscosity is determined in a rotational rheometer using a cone-plate geometry at 20° C. at a shear rate of 50 1/s.

If the composition is provided as texturised product (pudding etc.) ready for consumption to be eaten with a spoon a viscosity of at least 350 mPa·s, preferably above 750 mPa·s, more preferably between 1000 and 4000 mPa·s. is preferred.

Therapeutical Uses and Methods:

The composition of the invention can be used in the treatment or prevention of diseases or for methods for the treatment or prevention of diseases associated with a nutritional status in diseased subject that differs from the nutritional status of a healthy subject.

In a preferred embodiment, the disease is an inflammatory bowel disease (e.g. Crohn's disease, ulcerative colitis, collagenous colitis, lymphocytic colitis, diversion colitis, Behçet's disease, indeterminate colitis). Other diseases or clinical conditions for which the methods and compositions of the invention are suitable include irritable bowel syndrome, type 2 diabetes, Parkinson disease, Alzheimer disease, cognitive decline/impairment, depression, critical care conditions.

Methods of Production:

A method for producing the above described composition is provided and comprises providing at least one of the above described nutrients, and adding optionally at least one further nutrient, said nutrients, for example, selected from the group consisting of one or more amino acids, fat, or carbohydrate, optionally adding a carrier or/and water.

Those skilled in the art will understand that they can freely combine all features of the present invention disclosed herein. In particular, features described for different embodiments of the present invention may be combined. Further advantages and features of the present invention are apparent from the figures.

The invention claimed is:

1. A method for manufacturing a nutritional composition for administration to a subject suffering from a disease characterized by distinctive nutritional requirements in the subject over a healthy subject, the method comprising:

a. determining in a sample of the subject suffering from the disease a profile of statuses of markers comprising direct and indirect markers indicating the nutritional profile of the subject, wherein each of the direct markers indicates an amount of a macronutrient or micronutrient, and each of the indirect markers are derived from the direct markers by quantifying a corresponding direct marker and quantifying one or more additional markers that indicate a status of the corresponding direct marker, at least one of the direct and indirect markers is selected from the group consisting of an amino acid marker, a fat marker, a carbohydrate marker, a nucleotide marker, an osmolyte marker, a peptide marker, a catabolism marker, a nitric synthase marker, and combinations thereof;

b. determining in a sample of the healthy subject a profile of the statuses of the same markers comprising the same direct and indirect markers determined in step a, at least one of the sample of the subject suffering from the disease or the sample of the healthy subject is a sample selected from the group consisting of whole blood, blood plasma, blood serum, red blood cells, urine, tissue biopsies, and combinations thereof;

c. comparing the profiles determined in steps a. and b., and determining distinctive nutritional requirements for nutrients comprising macronutrients and micronutrients in the subject suffering from the disease based on the comparison of the profiles determined in steps a. and b., wherein when a level of the markers determined in step a. is lower than a level of the same markers determined in step b., the distinctive nutritional requirements for the subject comprise a composition comprising the nutrients in an effective amount to enable a level of the nutrients in the subject suffering from the disease to match a level of the nutrients in the healthy subject; and d. manufacturing the composition comprising the nutrients in the effective amount to restore the nutritional profile of the nutrients in the subject suffering from the disease to or toward that of the healthy subject as determined in step b.

2. The method of claim 1, wherein in step a., the statuses of the markers is determined in a cohort of subjects suffering from the disease.

3. The method of claim 1, wherein in step b., the statuses of the markers is determined in a cohort of healthy subjects.

4. The method of claim 1, wherein the statuses of at least 10 markers are determined.

5. The method of claim 1, wherein the catabolism marker is selected from the group consisting of ammonia, urea, monomethyl, dimethylarginine, and combinations thereof.

6. The method of claim 1, wherein the markers further comprise an oxidative stress marker selected from the group consisting of 4-hydroxynonenal, malondialdehyde, nitrotyrosine, carbonylated proteins, total glutathione, reduced glutathione, oxidized glutathione, glutathione peroxidase activity, glutathione reductase activity, superoxide dismutase activity, catalase activity, and combinations thereof.

7. The method of claim 1, wherein the nitric synthase marker is selected from the group consisting of nitrite, nitrate, monomethyl arginine, asymmetric dimethylarginine, symmetric dimethylarginine, arginine, citrulline, ornithine, argininosuccinic acid, and combinations thereof.

8. The method of claim 1, wherein the amino acid marker comprises a marker of an amino acid selected from the group consisting of amino alanine, β-alanine, sarcosine, arginine, monomethylarginine, assymetric-dimethylarginine, symmetric dimethylarginine, asparagine, aspartic acid, citrulline, glutamic acid, glutamine, glycine, histidine, 1-methylhistidine, 3-methylhistidine, isoleucine, leucine, lysine, methionine, ornithine, phenylalanine, proline, serine, taurine, threonine, tryptophan, tyrosine, valine, hydroxyproline, ethanolamine, α-aminobutyric acid, β-aminoisobutyric acid, γ-aminobutyric acid, homocysteine, cysteine, γ-glutamylcysteine, cysteinyl-glycine, homocystine, cysteine, cystathionine, methionine sulfoxide, selenomethionine, methionine sulfoximine, selenocysteine, selenocystine, ergothioneine, N-formyl-L-methionine, S-adenosylhomocysteine, S-Adenosylmethioninamine, alpha-ketobutyric acid, 2-aminobutyric acid, 2-amino-3-ketobutyric acid, alpha-keto-beta-methylbutyric acid, alpha-ketoisovaleric acid, alpha-ketoisocaproic acid, alpha-keto-beta-methylvaleric acid, and combinations thereof.

9. The method of claim 1, wherein the markers further comprise a fatty acid marker selected from the group consisting of butyric C4:0, caproic C6:0, caprilic C8:0, capric C10:0, undecanoic C11:0, lauric C12:0, tridecanoic C13:0, myristic C14:0, pentadecanoic C15:0, palmitic C16:0, heptadecanoic C17:0, stearic C18:0, arachidic C20:0, heneicosanoic C21:0, behenic C22:0, lignoceric C24:0, myristoleic C14:1 n-5, cis-10-Pentadecenoic C15:1 n-5, palmitoleic C16:1 n-7, cis-10-heptadecenoic C17:1 n-7, elaidic C18:1 n-9 trans, oleic C18:1 n-9 cis, cis-11-Eicosenoic C20:1 n-9, erucic C22:1 n-9, nervonic C24:1 n-9, linoelaidic C18:2 n-6 trans, linoleic C18:2 n-6 cis, gamma-linolenic C18:3 n-6, alpha-Linolenic C18:3 n-3, cis-11,14-Eicosadienoic C20:2 n-6, cis-8,11,14-eicosatrienoic C20:3 n-6, cis-11,14,17-eicosatrienoic 20:3 n-3, arachidonic C20:4 n-6, cis-13,16-docosadienoic 22:2 n-6, cis-5,8,11,14,17-eicosapentanoic (EPA) C20:5 n-3, cis-4,7,10,13,16,19-Docosahexaenoic (DHA) C22:6 n-3 acid, lipoic acid, and combinations thereof.

10. The method of claim 1, wherein the markers further comprise an element marker of an element selected from the group consisting of lithium (Li), boron (B), magnesium (Mg), aluminium (Al), silicon (Si), phosphorous (P), sulfur (S), potassium (K), calcium (Ca), vanadium (V), chromium (Cr), manganese (Mn), iron (Fe), cobalt (Co), nickel (Ni), copper (Cu), zinc (Zn), arsenic (As), selenium (Se), bromine (Br), rubidium (Rb), strontium (Sr), molybdenum (Mo), tin (Sn), iodine (I), barium (Ba), titanium (Ti), sodium (Na), chlorine (Cl), and fluorine (F).

11. The method of claim 1, wherein the markers further comprise a vitamin marker of a vitamin or a metabolite thereof selected from the group consisting of vitamin B1, vitamin B2, vitamin B3, nicotinamide, methylnicotinamide, nicotinuric acid, choline, vitamin B5, vitamin B6, pyridoxal phosphate, pyridoxic acid, vitamin B8, vitamin B9, methyl tetrahydrofolic acid, vitamin B12, hydroxycobalamin, adenosylcobalamin, and combinations thereof.

12. The method of claim 1, wherein the nucleotide marker comprises a marker of a nucleotide selected from the group consisting of inosine 5'monophosphate, adenosine 5'monophosphate, cytidine 5'monophosphate, guanosine 5'-monophosphate, inosine 5'monophosphate, uridine 5'monophosphate, and combinations thereof.

13. The method of claim 1, wherein the osmolyte marker is selected from the group consisting of trimethylamine N-oxide, dimethylsulfoniopropionate, trimethylglycine, sarcosine, betaine, glycerophosphorylcholine, myo-inositol, and combinations thereof.

14. The method of claim 1, wherein the markers further comprise a phytonutrient marker of a phytonutrient selected from the group consisting of carotenoids, ellagic acid, flavonoids, chlorogenic acids, resveratrol, glucosinolates, phytoestrogens, or a combination thereof.

15. The method of claim 1, wherein the peptide marker comprises a marker of a peptide selected from the group consisting of reduced gluthatione, oxidized glutathione, and combinations thereof.

16. The method of claim 1, wherein the indirect marker is selected from the group consisting of combinations of nutrients and micronutrients, biomarkers of nutrients or micronutrients, metabolites of nutrients or micronutrients, catabolites of nutrients or micronutrients, physiological states, ratios between nutrients and micronutrients, ratios between micronutrients, determinations of functional markers, and combinations thereof.

17. The method of claim 16, wherein the functional markers comprise measurement of an activity selected from the group consisting of erythrocyte transketolase activity, erythrocyte glutathione reductase activity, oxidative stress status, nitric oxide synthase activity, and combinations thereof.

18. A method of treating a human subject suffering from a disease characterized by distinctive nutritional requirements in the human subject over a healthy subject, the method comprising:

a. determining in a sample of the human subject suffering from the disease a profile of statuses of direct and indirect markers indicating the nutritional profile of the human subject, wherein each of the direct markers indicates an amount of a macronutrient or micronutrient, and each of the indirect markers are derived from the direct markers by quantifying a corresponding direct marker and quantifying one or more additional markers that indicate a status of the corresponding direct marker, at least one of the direct and indirect markers is selected from the group consisting of an amino acid marker, a fat marker, a carbohydrate marker, a nucleotide marker, an osmolyte marker, a peptide marker, a catabolism marker, a nitric synthase marker, and combinations thereof;

b. determining in a sample of the healthy subject a profile of the statuses of the same markers comprising the same direct and indirect markers determined in step a, at least one of the sample of the subject suffering from the disease or the sample of the healthy subject is a sample selected from the group consisting of whole blood, blood plasma, blood serum, red blood cells, urine, tissue biopsies, and combinations thereof;

c. comparing the profiles determined in step a. and b., and determining distinctive nutritional requirements for nutrients comprising macronutrients and micronutrients in the human subject suffering from the disease based on the comparison of the profiles determined in steps a. and b., wherein when a level of the markers determined in step a. is lower than a level of the same markers determined in step b., the distinctive nutritional requirements for the subject comprise a composition comprising the nutrients in an effective amount to enable a level of the nutrients in the subject suffering from the disease to match a level of the nutrients in the healthy subj ect;

d. providing the composition to restore the nutritional profile of the nutrients in the human subject suffering from the disease; and e. administering the composition to the human subject suffering from the disease.

* * * * *